United States Patent [19]

Hewes, Jr.

[11] Patent Number: 4,516,574

[45] Date of Patent: May 14, 1985

[54] TOOL FOR CASTRATING ANIMALS BY SEVERING THE SPERMATIC CORD BY SEARING OR CAUTERIZATION

[76] Inventor: Francis W. Hewes, Jr., Toponas, Colo. 80472

[21] Appl. No.: 485,667

[22] Filed: Apr. 18, 1983

[51] Int. Cl.³ .................. A61B 17/32; A61B 17/38
[52] U.S. Cl. .................. 128/303.1; 128/306; 30/140; 219/230
[58] Field of Search .......... 128/303.1, 303.14, 303.17, 128/306; 30/140; 219/230

[56] References Cited

U.S. PATENT DOCUMENTS

| | | |
|---|---|---|
| 1,586,645 | 6/1926 | Breman . |
| 2,012,937 | 9/1935 | Beuoy .................... 219/230 |
| 3,117,578 | 1/1964 | Helbling ................. 128/303.14 |
| 4,046,148 | 9/1977 | Meador ................... 30/140 X |

FOREIGN PATENT DOCUMENTS

| | | | |
|---|---|---|---|
| 40469 | 8/1887 | Fed. Rep. of Germany ...... 128/306 |
| 639545 | 2/1979 | U.S.S.R. .................... 128/303.14 |

Primary Examiner—Lee S. Cohen
Attorney, Agent, or Firm—Sheridan, Ross & McIntosh

[57] ABSTRACT

A veterinarian's tool for castrating animals with which all of the castrating operations can be performed with a single tool held in one hand of the operator, the tool operating to sever the spermatic cord by searing or cauterization and comprising a pair of arms pivotally connected together to operate in scissor-like manner, one arm having a cutting blade at its upper end for making an opening in an animal's scrotum, the other arm having a "V" or fork at its upper end for stripping back the covering of the spermatic cord after it has been pulled out of the animal's body, and a heating element on one of the arms, the arms cooperating upon closing to hold the animal's spermatic cord against the heating element until the cord is severed by searing or cauterization.

7 Claims, 8 Drawing Figures

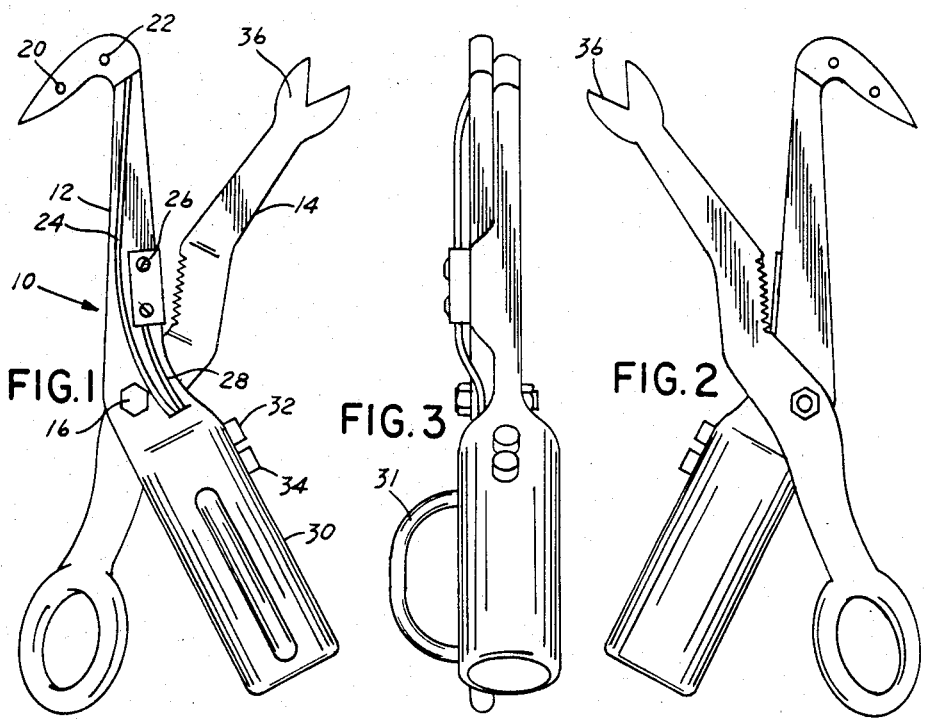
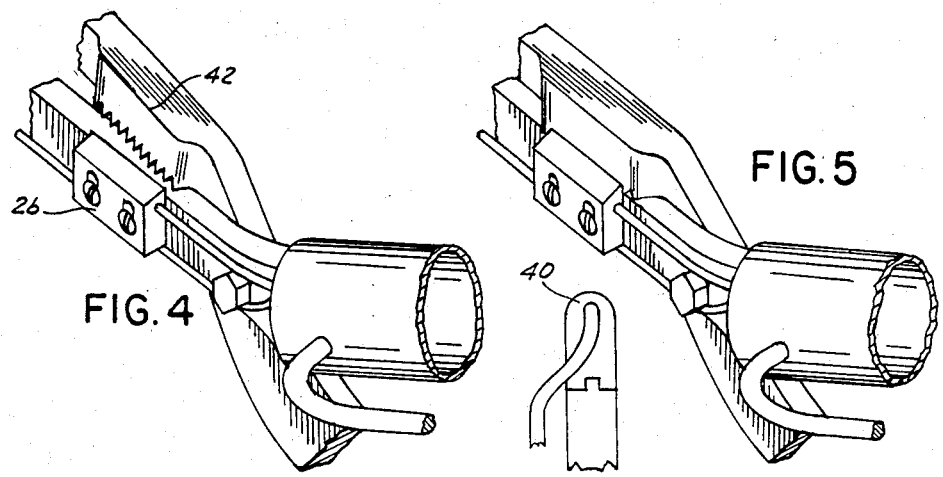
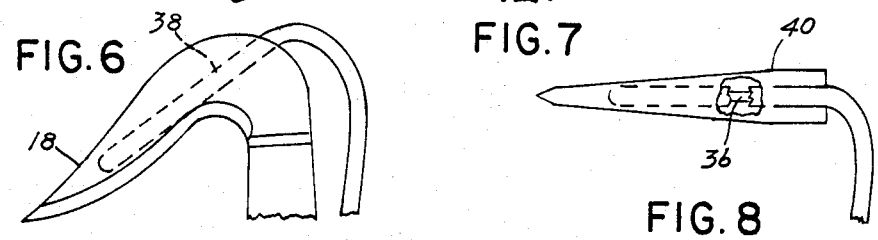

TOOL FOR CASTRATING ANIMALS BY SEVERING THE SPERMATIC CORD BY SEARING OR CAUTERIZATION

TECHNICAL FIELD

This invention lies in the field of veterinary instruments and, particularly, in the field of castrating devices.

BACKGROUND ART

The prior art is represented generally by U.S. Pat. Nos. 881,117; 1,957,159; 1,978,124; 2,476,895; 2,966,911 and 4,033,352. These patents disclose animal castrating devices operating essentially by cutting or crushing the spermatic cords. The use of heat to sever the cords by searing and cauterization is not disclosed. The simultaneous severing of the cords and cauterizing the remaining severed ends is not disclosed. A device for simultaneously severing an animal's horn by cutting and cauterizing the area from which the horn is severed is disclosed in U.S. Pat. No. 4,345,377.

DISCLOSURE OF THE INVENTION

The invention is a castrating device which simultaneously severs the spermatic cords by searing with heat and cauterizes the ends remaining in the body. It provides a single tool for cutting an opening in the scrotum, stripping the covering of the cord back into the body after it has been pulled from the scrotum, and then severing the cord and simultaneously cauterizing the end of the cord left in the body with heat. The operator can perform all of these functions with the tool held in one hand, thus leaving the other hand free for any necessary assist operations. Additionally, a tool is provided having a replaceable cutting element, an adjustable heating element and with which all of the castration steps can be performed with a single tool thus avoiding present disadvantages encountered in castration operations of having to perform separate operations with separate tools thus requiring changing tools.

The castration instrument is of scissor-like construction comprising first and second arms pivotally connected so that their ends can be opened and closed in scissor-like manner, the first arm supporting a cutting blade at its distal end for opening the scrotum of an animal, the second arm having a "V" or fork at its distal end for stripping the covering of the spermatic cord back into the body after the cord has been pulled from the body, the inner surfaces of said arms cooperating on closing in a sliding abutting relationship to hold and sever the spermatic cord of an animal by searing so that the cutting of the scrotum, stripping, and severing operations can be performed with one instrument held in one hand of the operator. Provision is made in the way of heating elements adjacent the cutting blade and the abutting surfaces of the arms for, respectively, cauterizing the wound in the scrotum and the severed end of the spermatic cord remaining in the body.

DESCRIPTION OF THE FIGURES

FIG. 1 is a top plan view of the castrating tool designed for use with the right hand;
FIG. 2 is a side elevational view;
FIG. 3 is a bottom plan view;
FIG. 4 is a detail taken of the central area of the tool showing the abutting portions of the arms slightly apart;
FIG. 5 is a detail like FIG. 4 showing the abutting portions of the arms in sliding abutment;
FIG. 6 is a detail of the end of the arm supporting the cutting blade;
FIG. 7 is a detail like FIG. 6 showing the back of the area supporting the cutting blade; and
FIG. 8 is a detail like FIG. 6 showing the front of the area supporting the cutting blade.

BEST MODE FOR CARRYING OUT THE INVENTION

Referring now to the drawing, the castrating instrument indicated generally by the numeral 10 is comprised of arms 12 and 14 pivotally connected by screw or bolt 16 for movement together and apart in a scissor-like manner. The arms 12 and 14 are preferably made of stainless steel with the lower or holding portions covered with rubber or other insulating material to protect the holder from electrical shock. The arms 12 and 14 may be made of plastic or other dielectric material.

The distal end of arm 12 is split to hold a removable cutting blade 18 (FIG. 6) which is held in place between the portions formed by the split by bolts, screws or rivets 20 and 22. A sheath 24 of insulating material holds two electrically conducting wires connected to the cutting blade 18 and a battery or other source of electrical power.

The cutting blade is heated by electrical power for cauterizing the wound made by it in the scrotum. The upper portion of arm 12 can be made hollow and the sheath 24 encased in it.

For severing the spermatic cord of the animal, a metal heating element 26 is suitably mounted on the interior edge of the central portion of arm 12 as shown. The heating element is mounted to be adjustable by means of bolts secured to arm 12 extending into slots in the heating element as shown.

A sheath 28 of insulating material encases two electrical conductors connecting the heating element 26 to a source of electrical power for heating it to sever the spermatic cord by cauterization.

The lower holding portion of arm 12 is constructed as a hollow case 30 for holding batteries as one source of electrical power for cutting blade 18 and heating element 26. The batteries may be separated from the instrument and carried on the belt of the user, for example. Obviously, other sources of electrical power could be used, such as, ordinary 110 volt electrical current connected to the cutting blade 18 and heating element 26 by extension cords. For stability, a thumb support 31 is mounted on case 30. Switch members 32 and 34 are connected into the circuits between the cutting blade 18 and the battery and the heating element 26 and the battery for switching the current on and off.

The upper portion of arm 14 is provided at its upper end with a "V" or fork 36 for stripping or pushing the cover on the spermatic cord back into the body after the cord has been pulled from the body and before it is severed.

If the arms 12 and 14 are made of metal, the blade 18 can be made integral with arm 12 but a separate removable blade is preferred. The heating element 26 can also be dispensed with and the metal arm is heated electrically for the searing, but a separate heating element is preferred. The arms 12 and 14 can be made of plastic or other dielectric material with a metal part cooperating with heating element 26 being provided on arm 14 adjacent the heating element when the arms are closed.

A heater element 38 for blade 18 is shown schematically in FIG. 6. A removable head portion 40 for holding the blade 18 and its heater element 36 is shown in FIG. 7 attached to the upper portion of arm 12 by suitable means such as screws.

The arms 12 and 14 are adjusted by the bolt 16 so that as they are brought together the abutment portion 42 of arm 14 and the adjacent surface of heating element 26 are in sliding abutting relationship to momentarily hold and sever the spermatic cord by cauterization. For convenience the arms are constructed so that they scissor slightly beyond their sliding abutment point after the cord is severed. The face of portion 42 is preferably serrated to provide a better grip on the cord.

The castrating operation performed with the instrument held in the right hand is as follows. As the animal is restrained from movement, a slit in the scrotum is made above one testicle with the heated cutting blade 18 leaving the cut area cauterized. The testicle is then grasped with the left hand and pulled from the scrotum with the spermatic cord still attached to the body and testicle. The testicle is pulled outwardly with the left hand until a substantial portion of the spermatic cord is outside the body. With the testicle still held in the left hand of the operator, its covering is stripped or scraped from the cord back into the body by means of the "V" at the end of arm 14. The cord, still attached to the testicle held in the left hand of the operator, is then moved into the cauterizing area between heating element 26 and the adjacent abutting area 42 of arm 14 where it is held firmly against the heating element 26. The arms 12 and 14 are constructed and adjusted with bolt 16 so that the cord is held firmly between their abutment areas and the cord gradually moved into the cauterization area. The switch 32 or 34, whichever is appropriate, is then activated to bring electrical current to the heater element to sever the cord by searing leaving the end of the cord still attached to the body cauterized. The switch can be activated prior to the operation as convenient.

The instrument can be constructed for use by a left-handed operator. The arms 12 and 14 are interchangeable in that either one can be modified to hold the various described elements, such as, cutting blade 18, heating elements 26 and 38, case 30, fork 36 and abutment portion 42, etc. A spring may be biased between the arms 12 and 14 either forcing the arms open or closed as desired.

The tool is particularly useful for castrating calves although it is by no means restricted to this use.

What is claimed is:

1. A tool for castrating animals operating to sever the spermatic cord at least partly by searing or cauterization, comprising:
   (a) a pair of arms pivotally connected together to operate in scissor-like manner;
   (b) means on one of said arms for stripping the covering of the spermatic cord of an animal after the cord has been pulled out of the animal's body during castration,
   (c) a heating area on one of said arms cooperating with said other arm upon closing of the arms to contact the spermatic cord of an animal between said arms to sever the cord at least partly by searing or cauterization, and (d) means for connecting said heating area to a source of energy.

2. The tool of claim 1 in which said means for stripping is a "V" or fork at the end of said one of said arms.

3. The tool of claim 1 including a cutting surface on one of said arms for cutting an opening in the scrotum of an animal.

4. The tool of claim 3 in which said cutting surface is a blade.

5. The tool of claim 4 in which said blade is removable.

6. A tool for castrating animals by which the spermatic cords are severed by searing or cauterizing comprised of:
   (a) a pair of arms pivotally connected together at a pivot point to operate in scissor-like manner resulting in a pair of arm sections on each side of said pivot point, one pair of arm sections having distal ends distal to said pivot point adapted to support a cutting blade or a fork;.
   (b) a cutting blade at said distal end of one of said arm sections for making an opening in the scrotum of an animal;
   (c) a "V" or fork on said distal end of said other arm section for stripping the covering of the spermatic cord of an animal after the cord has been pulled out of the animal's body,
   (d) a heating element on one of said arms cooperating with said other arm upon closing of the arms to contact the spermatic cord of an animal to sever the cord by searing or cauterization, and
   (e) means for connecting said heating element to a source of energy.

7. In a castrating tool comprising a pair of arms pivotally connected together at a pivot point to open and close in scissor-like manner resulting in a pair of arm sections on each side of said pivot point, one pair of arm sections having distal ends distal to said pivot point adapted to support a cutting blade or a fork, one of said arm sections having a cutting blade at its distal end for making an opening in the scrotum of an animal, the improvement which comprises a heating element on one of said arms cooperating with the other of said arms upon closing of the arms to contact the spermatic cord of an animal during castration to sever the cord by searing or cauterization, means for connecting said heating element to a source of energy, and a "V" or fork at said distal end of the other of said arms for stripping the covering of the spermatic cord of an animal after the cord has been pulled from the animal's body during castration.

* * * * *